United States Patent [19]

Gould et al.

[11] Patent Number: 4,462,245
[45] Date of Patent: Jul. 31, 1984

[54] APPARATUS FOR TESTING ABRASION RESISTANCE OF PRINTED SURFACES

[75] Inventors: Richard J. Gould, St. Paul; George M. Seiter, Golden Valley, both of Minn.

[73] Assignee: Champion International Corporation, Stamford, Conn.

[21] Appl. No.: 439,893

[22] Filed: Nov. 8, 1982

[51] Int. Cl.³ .............................................. G01N 3/56
[52] U.S. Cl. ......................................................... 73/7
[58] Field of Search ............................................. 73/7

[56] References Cited

U.S. PATENT DOCUMENTS

| | | | |
|---|---|---|---|
| 1,581,215 | 4/1926 | Kobin | 73/7 |
| 2,221,964 | 11/1940 | Verdier | 73/7 |
| 2,734,375 | 2/1956 | Galbraith et al. | 73/7 |
| 3,087,326 | 4/1963 | MacDonnell | 73/7 |

Primary Examiner—S. Clement Swisher
Attorney, Agent, or Firm—Evelyn M. Sommer; John H. Mulholland

[57] ABSTRACT

Apparatus for testing the abrasion resistance of a printed area on a carton which is also subjected to flexing during the abrasion process. The apparatus includes means for holding the two carton samples in proximity to each other while one sample is oscillated over and abraded with the other. One of the samples is provided with a raised center portion to simulate flexing of the carton samples as they are abraded.

2 Claims, 4 Drawing Figures

APPARATUS FOR TESTING ABRASION RESISTANCE OF PRINTED SURFACES

BACKGROUND OF THE INVENTION

1. Field Of The Invention:

This invention relates to improvements in apparatus for testing abrasion resistance of printed surfaces, and more particularly, to an apparatus to simulate abrasion forces on an ink printed and coated carton to predetermine the quality of various inks which can be used on a paperboard carton surface.

2. Description Of The Prior Art:

In the art of printing generally and more particularly in the art of printing paperboard cartons it is often desirable to predetermine how a particular batch of ink will react when the ink is applied or printed on a particular carton and the carton subjected to different conditions of abrasion, in the presence or absence of moisture. Heretofore it has been possible to somewhat pretest inks for this purpose and how a particular carton printed with a particular ink will react to various conditions encountered in the handling of a carton by the use of apparatus that is commonly referred to as a "Sutherland Rub Tester", and which is shown in detail in U.S. Pat. No. 2,734,375, issued Feb. 14, 1956, which disclosure is incorporated herein. Generally, this apparatus seeks to reproduce identical abrasive acts on a sample of a paperboard to be used in a carton and printed with the ink to be tested. The results of the abrasion tests are compared with results obtained with different inks and different samples of paperboard that have been submitted to identical tests. This apparatus provides means for attempting to simulate and reproduce the actual abrasion forces encountered on the test sample. That is, the sample is subjected to the same number of abrasive strokes applied at the same pressure. The apparatus is adjustable for varying the number of abrasive strokes and their pressure as different properties of the sample and the characteristics of the sample to be tested are changed.

However, the apparatus disclosed in U.S. Pat. No. 2,734,375 does not employ any means to simulate the flexing of the carton while the surface thereof is being rubbed, scuffed or abraded, and therefore does not supply an accurate simulation of the abrasion forces normally encountered by the printed carton surface during handling and shipping, particularly where the carton contains a product that has a pressure point contact with the carton surface.

SUMMARY OF THE INVENTION

Accordingly, the "Sutherland Rub Tester" as disclosed in U.S. Pat. No. 2,734,375 is modified by placing a metal shim under a bottom carton test sample while the surface of the sample is being abraded by contact with a top or overlying test carton surface. This causes the sample carton surfaces to flex in and out in a bellows-type motion at spaced pressure points on both sides of the shim. This flexing, while abrading the carton samples, better simulates the forces exerted on a carton which contains a product that has pressure point contact in addition to the normal rubbing or abrading forces between the carton samples. Therefore, the objects of this invention are:

First, to provide an apparatus that will accurately reproduce and simulate abrasion forces encountered on a sample of printed paperboard that are identical in pressure and duration.

Second, to provide a testing apparatus for identically reproducing various preselected rubbing operations between a printed surface and the surface of a strip of test paper.

Third, to provide means for testing the abrasion resistance properties of inks on various papers and under various conditions by reproducing identical abrasion forces and conditions and comparing the results of various tests.

Fourth, to provide apparatus for testing abrasion resistance properties and other properties of printed surfaces which will permit printers to predetermine the quality of various inks when used on various surfaces to be printed.

BRIEF DESCRIPTION OF THE DRAWINGS

Further objects and advantages of the invention will become apparent from the following description and claims and from the accompanying drawings, wherein:

DETAILED DESCRIPTION OF THE PREFERRED EMBODIMENT

Figure 1:
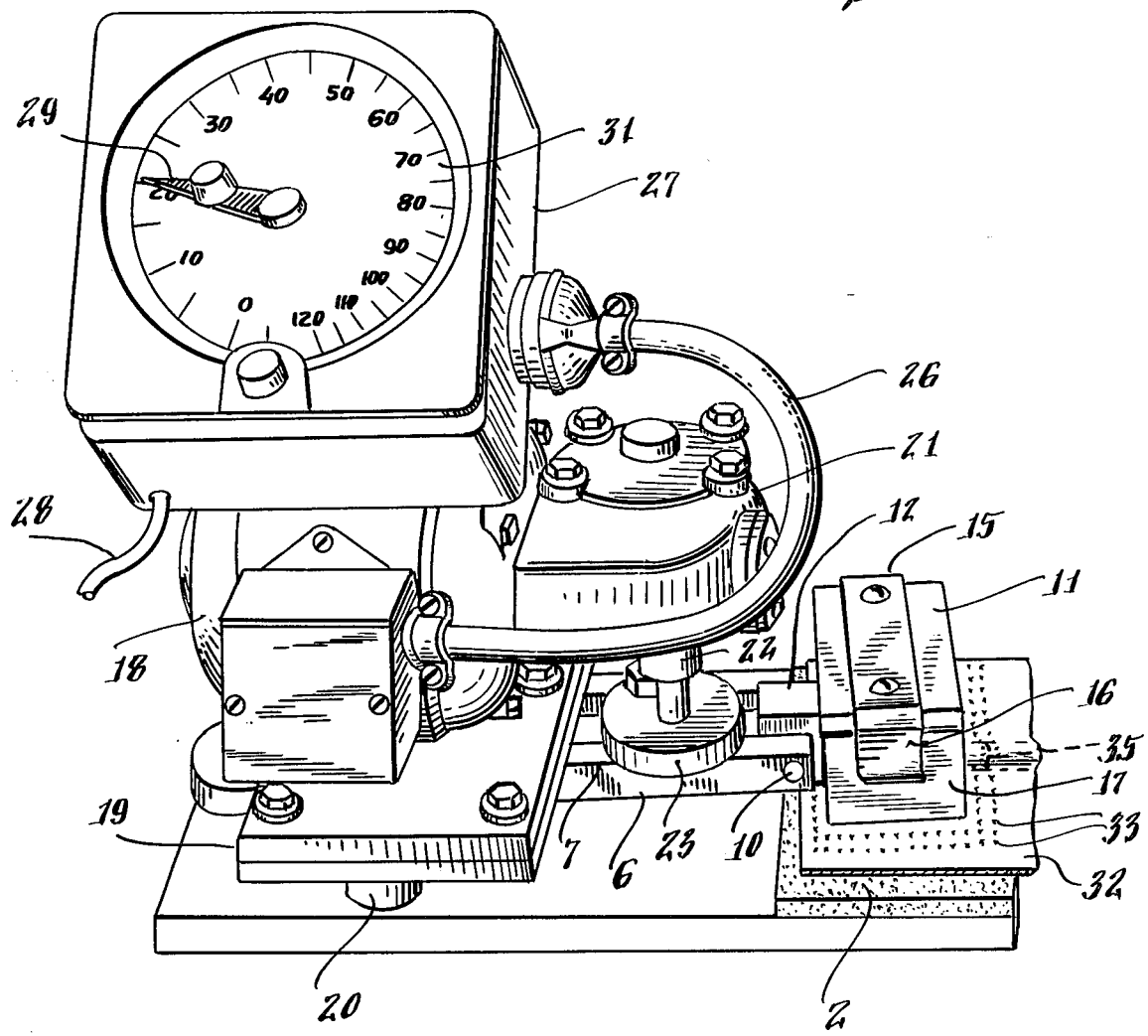
FIG. 1 is a perspective view of the testing apparatus in operative position.
Figure 2:
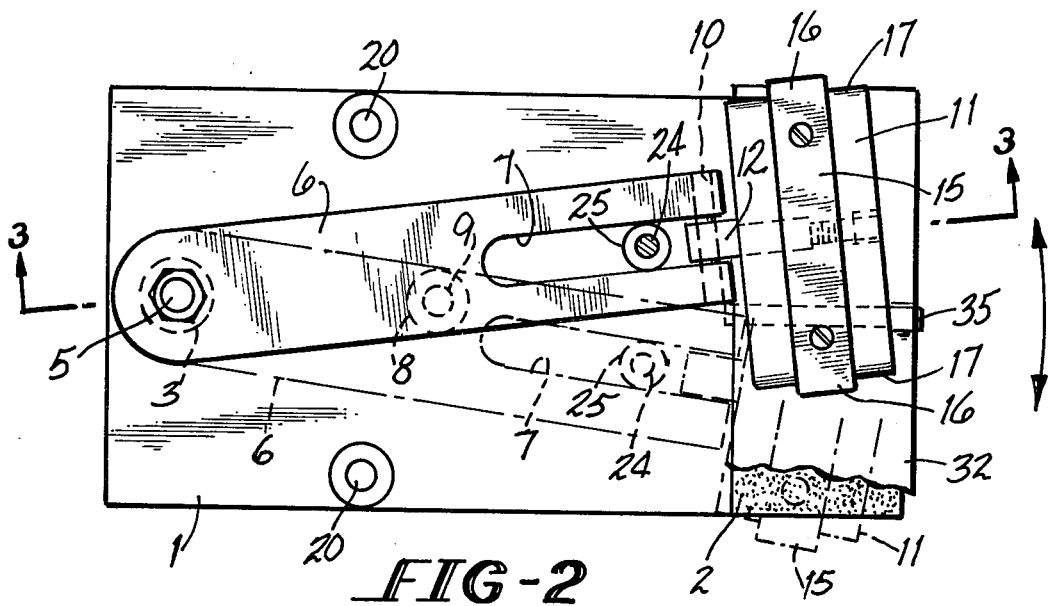
FIG. 2 is a plan view of the base and operating arm of the apparatus with the driving motor and timing apparatus removed.
Figure 3:
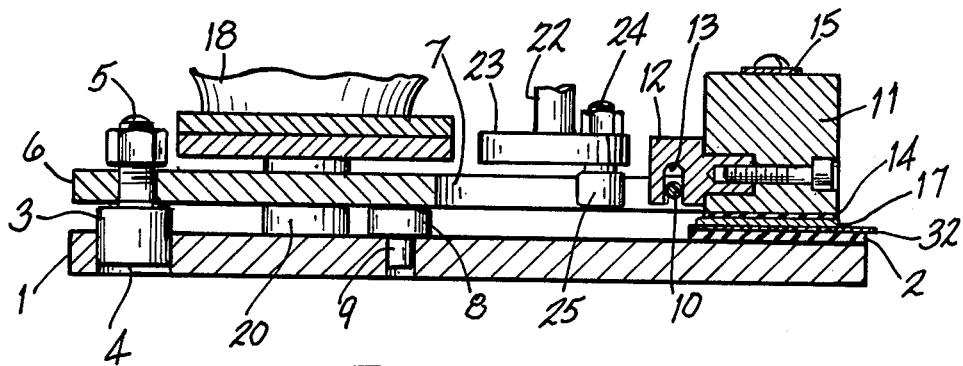
FIG. 3 is a fragmentary vertical, longitudinal cross sectional view through the base taken along the plane of the line 3—3 in FIG. 2.

Referring now to the drawings in detail, wherein like numerals indicate like elements throughout the several views, the testing apparatus comprises a flat base plate 1 desirably of metal. The right end of the plate as viewed in the drawing is provided with a relatively thin pad 2 of deformable material such as sponge rubber. The pad is of uniform thickness and perfectly flat on its surfaces. A bushing 3 is rotatably received in a hole 4 at the left end of the plate and carries an upstanding stud 5 to which the left end of an arm 6 is securely fastened. The arm 6 extends longitudinally over the plate 1 to adjacent the pad 2 and is vertically slotted as at 7 from its swinging end. A flat pad or bearing 8 secured to the plate 1 by a depending peg 9 slidably supports the arm intermediate of its ends. A pin 10 extends across the open end of the slot 7.

Figure 4:
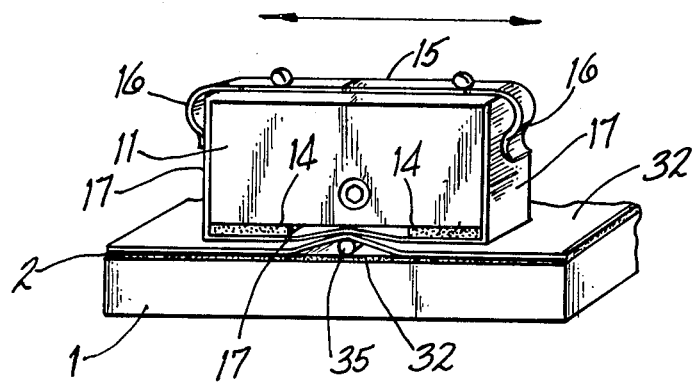
FIG. 4 is a perspective view of an abrasion block employed with the apparatus.

Adapted to coact with the arm 6 and the pad 2 is a block 11. The block 11 has secured to one side an ear 12 that is vertically slotted as at 13 from the underside to hook over the pin 10 with the ear projecting into the slot 7 of the arm. The slot 13 is deep enough so that the block is not supported vertically by the pin. The undersurface of the block is provided with flat shoes 14 at each end which consist of small rectangles of deformable material such as sponge rubber. Spring grip 15 is secured to the top of the block with downturned ends 16 extending over the ends of the block to springably engage and hold the ends of strips 17 of test paper as illustrated in FIGS. 1 and 4.

In order to oscillate the arm 6 and the block connected to the end thereof, the apparatus is provided with a motor 18. The motor is mounted on a base plate 19 and the base plate is supported in spaced relationship above the arm 6 by a pair of posts 20 secured to the base plate 1 on opposite side of arm 1. The motor carries a gear box or transmission 21 that projects over the right edge of the base plate 19 so that a crank shaft 22 depending from the transmission will be positioned over the arm 6. The crank shaft carries a crank wheel 23 and the wheel carries a depending crank pin 24 eccentrically mounted on the wheel. A bearing 25 carried on the pin 24 slidably and drivingly engages the sides of the slot 7 in the arm.

The motor 18 is supplied with energy through the cable 26 from a timing device 27 mounted on top of the motor. The timing device is a commercially available article and it is believed sufficient to an understanding of the invention to point out that the timing device is an adjustably timed switching mechanism that will energize cable 26 from a power source such as the cable 28 during a predeterminable adjustable timed interval. The timing device includes an adjusting lever 29 which can be moved to vary the interval during which the cable 26 will be energized and a control button 30 adapted to start the timing device through its timed interval. The lever 29 coacts with a calibrated scale 31 so that the operator can select the desired interval of operation of the motor 18. The scale 31 may be calibrated in seconds and with the rotational speed of the motor 18 and the gear ratio of the transmission 21 known this may be converted or calculated into a predeterminable number of oscillations of the arm 16 and block 11. More desirably the scale 31 is calibrated directly in the number of oscillations of the arm and block. It is pointed out that the motor 18 is relatively large and of sufficient capacity with respect to the load imposed by the block 11 to practically instantaneously bring the speed of oscillation of the arm and block up to the full rated speed of the motor.

In operating the apparatus of the invention a sample piece of paperboard 32 is imprinted with the ink to be tested as at 33 and after the ink has dried, the sample is placed on the pad 2 where the rubber like character of the pad retains the sample in place. A shim 35, such as a ⅛ inch O.D. cylindrical rod is placed beneath the sample 32 on the center of pad 2 and extends along the width of the pad and sample. The test block 11 is then fitted with a strip of test paperboard or cardboard 17 and engaged with the pin 10 so that the test strip 17 is pressed at a given and accurately reproducible pressure against the printed area 33. The lever 29 is adjusted to a reproducible number of strokes and the control button 30 actuated to oscillate the block 11 a given number of times causing the samples 17 and 32 to abrade along inked surface 33, while the samples are bowed or flexed in and out in bellows-like fashion at opposite sides of the diameter of the shim 35, which causes the spaced flexure or pressure points. This simulates the forces applied between abrading cartons, where one of the cartons will contain a product having a pressure point contact with the carton surface. It is pointed out that the test strips 17 and printed area 33 may be wet or dry as desired to simulate conditions to which the carton and ink will be subjected. Further, the shim 35 may be directly incorporated into the pad 2 or a sliding shim could be used that would move a certain distance under lateral pressure. After the test, the condition of the surface of the sample 32 and the test strip 17 can be observed and recorded and the samples filed for comparison for prior or later test under identical conditions.

What is claimed is:

1. An apparatus for testing abrasion resistance of printed paperboard surfaces which includes relative straight line reciprocative movement between a lower flat plate with a lower deformable surface pad thereon and an upper block having upper deformable members with a space therebetween on the lower surface thereof, which apparatus includes:

means for securing an upper paperboard sample on said upper block so as to overlie said upper deformable members and span the space therebetween, means for securing a lower paperboard sample strip on said lower deformable surface pad, and rigid shim means mounted behind and under said lower paperboard sample in a location and position in said space between said upper deformable pads thereby to create a flexing bellows-like motion in said samples in the space between said upper deformable members as they reciprocate opposite and relative to each other and rub against each other.

2. The apparatus of claim 1 in which said shim is a cylindrical rod.

* * * * *